United States Patent [19] [11] Patent Number: 5,395,761
Hershberger et al. [45] Date of Patent: Mar. 7, 1995

[54] PLASMID PHKY334, AN EXPRESSION VECTOR FOR EK-BGH AND HOST CELLS TRANSFORMED THEREWITH

[75] Inventors: Charles L. Hershberger, New Palestine; Jeffrey L. Larson, Indianapolis, both of Ind.

[73] Assignee: Eli Lilly and Company, Indianapolis, Ind.

[21] Appl. No.: 801,164

[22] Filed: Nov. 27, 1991

[51] Int. Cl.[6] .................. C12N 1/21; C12N 15/70
[52] U.S. Cl. ..................... 435/252.33; 435/320.1
[58] Field of Search ............... 435/320.1, 252.33; 536/27

[56] References Cited

U.S. PATENT DOCUMENTS 4,874,703 10/1989 Jaskunas .................. 435/252.33

FOREIGN PATENT DOCUMENTS

0405858A2 1/1991 European Pat. Off. ..... C12N 15/67

OTHER PUBLICATIONS

Nishi et al., *Gene*, vol. 44, 1986, pp. 29-36.

*Primary Examiner*—Richard A. Schwartz
*Assistant Examiner*—James Ketter
*Attorney, Agent, or Firm*—Paul J. Gaylo; John E. Parrish

[57] ABSTRACT

Plasmid pHKY334, an expression vector for Met-Phe-Pro-Leu-(Asp)$_4$-Leu-BGH, and host cells containing plasmid pHKY334 are disclosed and claimed.

3 Claims, 4 Drawing Sheets

PLASMID PHKY334, AN EXPRESSION VECTOR FOR EK-BGH AND HOST CELLS TRANSFORMED THEREWITH

BACKGROUND OF THE INVENTION

Many prokaryotic and eukaryotic genes have been expressed at high levels in prokaryotes such as *Escherichia coli*. The general approach has been to use a multicopy cloning vector with a strong promoter and an efficient ribosome binding site for the transcription and translation of the cloned gene (Masui, Y., Coleman, J. and Inouye, M. (1983) in Experimental Manipulation of Gene Expression, ed. Inouye, M. (Academic, New York), pp. 15-32; Crowl, R., Seamans, C., Lomedico, P. and McAndrew, S. (1985) *Gene* 38:31-38). However, the level of gene expression with these vectors varies widely for different eukaryotic genes. Low-level expression has been attributed to protein degradation by *E. coli* proteases (Emerick, A. W., Bertolani, B. L., BenBassat, A., White, T. J. and Koñrad, M. W. (1984) *Bio/Technology* 2:165-168) or to inefficient translation initiation of mRNAs containing heterologous gene sequences (Ray, P. N. and Pearson, M. L. (1974) *J. Mol. Biol.* 85:163-175; Ray, P. N. and Pearson, M. L. (1975) *Nature* (London) 253, 647-650; Kelley, R. L. and Yanofsky, C. (1982) *Proc. Natl. Acad. Sci. USA* 79:3120-3124; Nagai, K. and Thogersen, H. C. (1984) *Nature* (London) 309, 810-812; Varadarajan, R., Szabo, A. and Boxer, S. G. (1985) *Proc. Natl. Acad. Sci. USA* 82:5681-5684). Several studies suggested that the efficiency of translation initiation depends on the degree of complementarity between the Shine-Dalgarno (SD) sequence and the 16S rRNA, the distance between the SD sequence and the initiation codon, and the nucleotide sequence of this "window" region (Shine, J. and Dalgarno, L. (1975) *Nature* (London) 254, 34-38; Gold, L., Pribnow, D., Schneider, T., Shineding, S., Singer, B. S. and Stormo, G. (1981) *Annu. Rev. Microbiol.* 35: 365-403; Stromo, G. D., Schneider, T. D. and Gold, L. M. (1982) *Nucleic Acids Res.* 10:2971-2996; Kozak, M. (1983) *Microbiol. Rev.* 47:1-45; Hui, A., Hayflick, J., Dinkelspiel, K. and deBoer, H. A. (1984) *EMBO J.* 3:623-629; Shepard, M. G., Yelverton, E. and Goeddel, D. V. (1982) *DNA* 1:125-131; deBoer, H. A., Hui, A., Comstock, L. J., Wong, E. and Vasser, M. (1983) *DNA* 2:231-235; Whitehorn, E. A., Livak, K. J. and Petteway, S. R., Jr. (1985) *Gene* 36:375-379). There is evidence that the translational efficiency also depends on the sequence of the 5' untranslated region of the mRNA outside the SD sequence and the 5' end of the protein coding region (Stanssens, P., Remaut, E. and Fiers, W. (1985) *Gene* 36:211-223; Roberts, T. M., Kacich, R. and Ptashne, M. (1979) *Proc. Natl. Acad. Sci. USA* 76:760-764; Gold, L., Stormo, G. and Saunders, R. (1984) *Proc. Natl. Acad. Sci. USA* 81:7061-7065) and the 3' untranslated region of the mRNA.

To reconcile these observations, it has been proposed that translation is inhibited when local secondary structures form with regions containing the SD sequence and/or the AUG start codon such that the ribosomes cannot initiate translation (Gheysen, D., Iserentant, D., Derom, C. and Fiers, W. (1982) *Gene* 17:55-63; Iserentant, D. and Fiers, W. (1980) *Gene* 9:1-12; Schwartz, M., Roa, M. and Debarbouille, M. (1981) *Proc. Natl. Acad. Sci. USA* 78:2937-2941; Hall, M. N., Gabay, J., Debarbouille, M. and Schwartz, M. (1982) *Nature* (London) 295, 616-618; Das, A., Urbanowski, J., Weissbach, H., Nestor, J. and Yanofsky, C. (1983) *Proc. Natl. Acad. Sci. USA* 80:2879-2883; Berkhout, B. and van Duin, J. (1985) *Nucleic Acids Res.* 13:6955-6967). The formation of such secondary structures may explain failures to express methionyl bovine growth hormone (Met-bGH) with its native codons at high levels (George, H. J., L'Italien, J. J., Pilacinski, W. P., Glassman, D. L. and Krzyzek, R. A. (1985) *DNA* 4:273-281; Seeburg, P. H., Sias, S., Adelman, J., deBoer, H. A., Hayflick, J., Jhurani, P., Goeddel, D. V. and Heyneker, H. L. (1983) *DNA* 2:37-45). To overcome this potential problem, Seeburg et al. have introduced several base changes into the 5' end of the bovine growth hormone (bGH) gene to create a sequence that is similar to the 5' end of the highly expressed human growth hormone (hGH) gene. Likewise, George et al. reported high-level expression (15% of total cell protein) after changing 13 codons in the 5' end of the bGH gene. These approaches are limited by the need to preserve the amino acid sequence of the protein. Polycistronic expression systems have been constructed to avoid the aforementioned limitations.

Features shared by polycistronic expression systems include a promoter to drive expression of the polycistronic mRNA, one or more ribosome binding sites, translation initiation sites for each cistron, and translation termination codons for each of the cistrons. The prior art teaches that expression levels of polypeptide products of interest are related to the strength of the promoter, the efficiency of ribosome binding site(s) on the polycistronic message, and the proper positioning of the translation initiation sites relative to the ribosome binding site(s).

Even with the construction of polycistronic expression systems, the expression of both bovine growth hormone and its derivatives such as EK-BGH (Met-Phe-Pro-Leu-(Asp)$_4$-Leu-BGH) remains problematic. Compounding the aforementioned problems is the structural instability of many expression vectors. Structural instability of recombinant DNA expression vectors results in DNA deletions and rearrangements that alter vector structure. This is a significant concern in large scale cultures grown to produce polypeptides encoded by these expression vectors. These vectors may be altered in a way that prevents expression of the encoded polypeptide. Thus, when the cultures are induced for expression of the polypeptide, a negative selective pressure toward a lack of polypeptide expression often results in an accumulation of the altered expression vectors.

In view of the above, regulatory agencies, such as the Food and Drug Administration, require full characterization of any recombinant DNA expression vectors that are utilized to produce polypeptide products of medicinal or veterinary utility. Evidence must be submitted to verify that the recombinant DNA expression vector is the same at the end of the fermentation as the expression vector from the original inoculum. Certification data includes structural and size analysis of the expression vector and verification of the nucleotide sequence that code for the desired product, and the regions flanking this coding sequence, especially flanking sequences that perform important functions, such as promoters.

Recombinant DNA vectors which utilize the *Escherichia coli* bacteriophage lambda pL promoter-operator region to enable transcription of an operably linked gene are often plagued by structural instability. When such vectors are examined at the end of the fermentation process, the structure of the vectors is often altered. The purpose of the present invention is to provide a stable expression vector while also providing regulatable transcription of the EK-BGH transcript.

The present invention provides an expression vector for production of EK-BGH which is stable, tightly regulated and achieve high levels of EK-BGH production. Thus, the present invention provides a significant advance in the area of production of EK-BGH and structurally related polypeptides.

SUMMARY OF THE INVENTION

The present invention provides pHKY334, a novel recombinant DNA expression vector.

BRIEF DESCRIPTION OF THE FIGURES

The figures appended hereto and described below are not drawn to scale.

DETAILED DESCRIPTION

Figure 4:
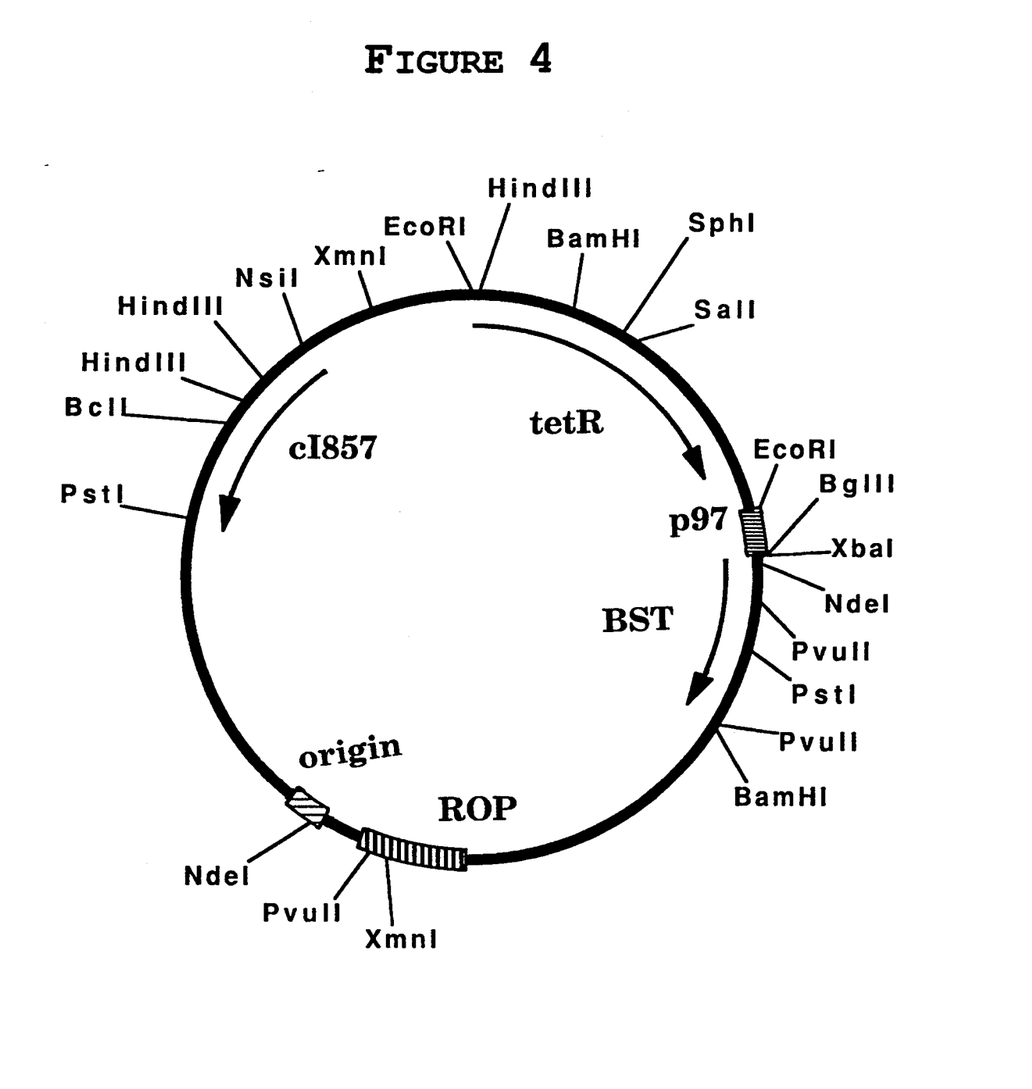
FIG. 4 is a restriction site and function map of plasmid pHKY334.

The recombinant DNA expression vector of the present invention is designated plasmid pHKY334. Plasmid pHKY334 was deposited as part of *E. coli* RV308/pHKY334 in the Northern Regional Research Laboratory, Peoria, Ill., on May 11, 1993 as NRRL B-21095. pursuant to the requirements of the Budapest Treaty. All restrictions regarding access to NRRL B-21095 will be removed following issuance of the present patent application and Applicants acknowledge and affirm the duty to replace the culture in the event it becomes non-viable or contaminated. A restriction site and function map of plasmid pHKY334 is provided in FIG. 4. Plasmid pHKY334 comprises a two cistron expression system which is driven by a lambda pL promoter, a tetracycline resistance gene which functions as a selectable marker, an origin of replication derived from plasmid pBR322, and a rop gene, which controls plasmid copy number in vectors comprising a pBR322 derived origin of replication.

Figure 1:
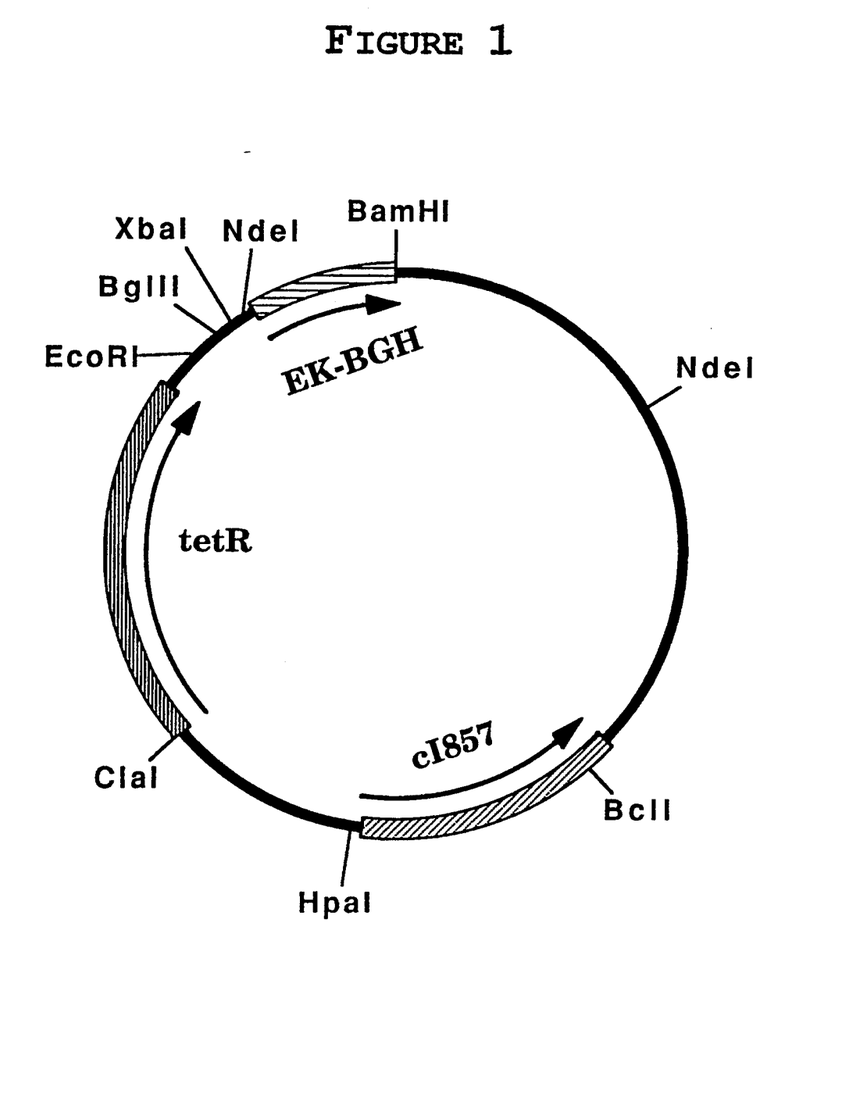
FIG. 1 is a restriction site and function map of plasmid pCZR125.

A comparison of plasmid pHKY334 with plasmid pL110 which is disclosed and claimed in U.S. Pat. No. 4,874,703, which issued Oct. 17, 1989, reveals several common structural features. Plasmid pL110 is an expression vector for a bovine growth hormone analog which is termed EK-BGH. Plasmid pCZR125 is also an EK-BGH expression vector. A restriction site and function map of plasmid pCZR125 is provided in FIG. 1. Despite common structural features between plasmid pCZR125 and plasmid pHKY334, it was necessary to culture host cells transformed with plasmid pCZR125 in the presence of a bacteriostatic or bactericidal concentration of an antibiotic when expression of EK-BGH was induced to prevent the accumulation of plasmids which had structural deletions and thus had ceased to express EK-BGH. The addition of bacteriostatic or bactericidal concentrations of antibiotics at the point at which EK-BGH production was induced was necessary due to the structural instability of plasmid pCZR125. By contrast, plasmid pHKY334 is stable upon induction of EK-BGH expression and thus does not require the addition of antibiotics to preclude the appearance of deletent or aberrant plasmids which no longer produce EK-BGH.

The increased stability of plasmid pHKY334 is attributable in part to modifications made to the phage lambda pL promoter, which is used to drive transcription of EK-BGH. The lambda pL promoter used to drive expression of EK-BGH was synthesized as taught in Example 3 subpart B. The synthesis of the lambda pL promoter was necessary to eliminate extraneous DNA sequences 5' to the lambda pL promoter. The presence of extraneous DNA sequences 5' to the lambda pL promoter contributed in part to the instability of plasmids such as plasmid pL110 and plasmid pCZR125. The extraneous DNA present in plasmids pL110 and pCZR125 but removed from plasmid pHKY334 was part of an inverted repeat of a tetracycline resistance gene present on the restriction fragment that was originally cloned from plasmid pBR322. This promoter is designated p97 in the accompanying figures.

Plasmid pHKY334 utilizes a tetracyline resistance gene, which was derived from plasmid pBR322 as a selectable marker. The tetracycline resistance gene is labeled tet R or tet in the accompanying figures. The origin of replication utilized in plasmid pHKY334 was also prepared from plasmid pBR322. The origin of replication is designated as either ori or origin in the accompanying figures. Plasmid pHKY334 comprises a rop gene which was prepared from plasmid pPR12, which is disclosed in U.S. Pat. No. 4,436,815, which issued Mar. 13, 1984. The rop gene controls plasmid copy number in plasmids containing a pBR322 derived origin of replication. Plasmid pHKY334 exists at a copy number of approximately 15 to 30 copies per cell. The rop gene is labeled rop in the accompanying figures. The temperature sensitive λpL repressor cI857 is used in all vectors disclosed herein and is labeled cI857 in the figures.

A number of host cells are suitable for use with plasmid pHKY334. *E. coli* K12 RV308 is the preferred host cell for pHKY334. *E. coli* K12 RV308 cells are available from the Northern Regional Research Laboratory in Peoria, Ill. under the accession number NRRL B-15624. *E. coli* MM294 (ATCC 31446), *E. Coli* C600 RM, which is also known as C600 (ATCC 33525) and *E. coli* JM109 (ATCC 53323) are also suitable host cells.

The restriction endonucleases and T4 DNA ligase used in the manipulation of the DNA fragments described in the Examples which follow were obtained from either Boehringer Mannheim Biochemicals, P.O. Box 50414, Indianapolis, Ind. 46250 or New England Biolabs, 32 Tozer Road, Beverly, Mass. 01915-5510. The source of materials is a matter of convenience. Unless otherwise indicated, reagent from either Boehringer Mannheim or New England Biolabs are equivalent and interchangeable for purposes of practicing the present invention.

The examples which follow are intended to further illustrate the present invention and are not intended as limiting the reasonable scope thereof.

EXAMPLE 1

Construction of pCZR125

A. Preparation of the 5.8 kb XbaI-BamHI Restriction Fragment of pL110

Plasmid pL110 is disclosed in U.S. Pat. No. 4,874,703, issued Oct. 17, 1989. The teachings of U.S. Pat. No. 4,874,703 are herein incorporated by reference.

Twenty-five μg of plasmid pL110 were digested to completion with 15 μl (150 units) of XbaI in a 500 μl reaction volume containing 60 mM Tris-HCl (pH 7.5), 10 mM MgCl$_2$, mM NaCl and 1 mM β-mercaptoethanol. Tris is Tris[hydroxymethyl]aminomethane. The mixture was incubated at 37° C. for one hour. The digested DNA was extracted two times with a mixture of phenol and chloroform (50:50) and the aqueous layer was recovered. The DNA was recovered from the aqueous layer by addition of 2.5 volumes of absolute ethanol and 0.1 volume of 3.0M sodium acetate. The DNA was collected by centrifugation and was resuspended in 50 μl of water.

The above DNA was partially digested with BamHI as follows. Fifty μl of the XbaI-digested DNA was mixed with 0.2 μl (2 units) of BamHI in a 150 μl reaction volume consisting of 10 mM Tris-HCl (pH 7.8), 7 mM MgCl$_2$, 150 mM NaCl and 6 mM β-mercaptoethanol. The mixture was incubated at 37° C. for 5 minutes. The sample was purified and recovered as described above and resuspended in 50 μl of TE (TE is 10 mM Tris-HCl (pH 7.4) and 1 mM ethylenediaminetetraacetic acid (EDTA)). Five μl of loading buffer (25% v/v glycerol, 0.05% w/v bromophenol blue, and 0.5% w/v xylene cyanole) were added to the sample and the digested DNA was fractionated on a 1% agarose gel by gel electrophoresis as described by Maniatis et al. at pages 150–172 (Maniatis et al., 1982, *Molecular Cloning: a Laboratory Manual*, Cold Spring Harbor Laboratory, Cold Spring Harbor, N.Y.). The agarose gel was stained with a dilute solution of ethidium bromide and the ~5.8 kb XbaI-BamHI restriction fragment was visualized under a 300 nm UV light. The portion of the gel containing this restriction fragment was recovered. The DNA was purified by mincing the gel slice, extracting it twice with phenol:chloroform (50:50) and ethanol precipitating the DNA as described above.

B. Preparation of XbaI-NdeI-linker

The following complementary DNA segments were synthesized on an automated DNA synthesizer (Applied Biosystems 380B) using β-cyanoethyl phosphoramidite chemistry:

5'-CTAGAGGGTATTAATAATGTATATTGATTTTAATAAGGA GGAATAATCA-3' (SEQ ID NO: 1)

5'-TATGATTATTCCTCCTTATTAAAATCAATATACATTATT AATACCCT-3' (SEQ ID NO: 2)

These single stranded DNA segments were conventionally purified and resuspended in water.

Five μg of each single stranded DNA segment were mixed and heated to 70° C. for five minutes. The mixture was cooled at room temperature for 30 minutes to allow the DNA segments to anneal.

The annealed DNA fragment was treated with 1 μl (10 units) of T4 polynucleotide kinase in 70 mM Tris-HCl (pH 7.6), 0.1M KCl, 10 mM MgCl$_2$, 5 mM DTT containing 0.2 mM adenine 5'-triphosphate in a total volume of 20 μl. The mixture was incubated at 37° C. for thirty minutes. The mixture was then incubated at 70° C. for 5 minutes and then cooled at room temperature.

C. Preparation of the Synthetic EK-BGH gene

The DNA fragment encoding the EK-BGH gene was synthesized in substantial accordance with the method of Example 1B. The gene encoding EK-BGH was constructed from 16 chemically synthesized pieces of single stranded DNA, ranging from 71 to 83 nucleotides in length, which, when annealed, comprise both complementary strands of the EK-BGH gene with NdeI and BamHI cohesive ends. The sequence of the synthetic EK-BGH gene is:

```
5'  -TATGTTCCCATTGGATGATGATGATAAGTTCCCAGCCATGTCCTT
     ||||||||||||||||||||||||||||||||||||||||||||||
     ACAAGGGTAACCTACTACTACTATTCAAGGGTCGGTACAGGAA

GTCCGGCCTGTTTGCCAACGCTGTGCTCCGGGCTCAGCACCTGCATCAGCTGGCTGCTGA
||||||||||||||||||||||||||||||||||||||||||||||||||||||||||||
CAGGCCGGACAAACGGTTGCGACACGAGGCCCGAGTCGTGGACGTAGTCGACCGACGACT

CACCTTCAAAGAGTTTGAGCGCACCTACATCCCGGAGGGACAGAGATACTCCATCCAGAA
||||||||||||||||||||||||||||||||||||||||||||||||||||||||||||
GTGGAAGTTTCTCAAACTCGCGTGGATGTAGGGCCTCCCTGTCTCTATGAGGTAGGTCTT

CACCCAGGTTGCCTTCTGCTTCTCTGAAACCATCCCGGCCCCCACGGGCAAGAATGAGGC
||||||||||||||||||||||||||||||||||||||||||||||||||||||||||||
GTGGGTCCAACGGAAGACGAAGAGACTTTGGTAGGGCCGGGGGTGCCCGTTCTTACTCCG

CCAGCAGAAATCAGACTTGGAGCTGCTTCGCATCTCACTGCTCCTCATCCAGTCGTGGCT
||||||||||||||||||||||||||||||||||||||||||||||||||||||||||||
GGTCGTCTTTAGTCTGAACCTCGACGAAGCGTAGAGTGACGAGGAGTAGGTCAGCACCGA

TGGGCCCCTGCAGTTCCTCAGCAGAGTCTTCACCAACAGCTTGGTGTTTGGCACCTCGGA
||||||||||||||||||||||||||||||||||||||||||||||||||||||||||||
ACCCGGGGACGTCAAGGAGTCGTCTCAGAAGTGGTTGTCGAACCACAAACCGTGGAGCCT

CCGTGTCTATGAGAAGCTGAAGGACCTGGAGGAAGGCATCCTGGCCCTGATGCGGGAGCT
```

-continued

```
|||||||||||||||||||||||||||||||||||||||||||||||||||||
GGCACAGATACTCTTCGACTTCCTGGACCTCCTTCCGTAGGACCGGGACTACGCCCTCGA

GGAAGATGGCACCCCCGGGCTGGGCAGATCCTCAAGCAGACCTATGACAAATTTGACAC
|||||||||||||||||||||||||||||||||||||||||||||||||||||||||||
CCTTCTACCGTGGGGGCCCGACCCGTCTAGGAGTTCGTCTGGATACTGTTTAAACTGTG

AAACATGCGCAGTGACGACGCGCTGCTCAAGAACTACGGTCTGCTCTCCTGCTTCCGGAA
|||||||||||||||||||||||||||||||||||||||||||||||||||||||||||
TTTGTACGCGTCACTGCTGCGCGACGAGTTCTTGATGCCAGACGAGAGGACGAAGGCCTT

GGACCTGCATAAGACGGAGACGTACCTGAGGGTCATGAAGTGCCGCCGCTTCGGGGAGGC
|||||||||||||||||||||||||||||||||||||||||||||||||||||||||||
CCTGGACGTATTCTGCCTCTGCATGGACTCCCAGTACTTCACGGCGGCGAAGCCCCTCCG

CAGCTGTGCCTTCTAG-3'
||||||||||||||||
GTCGACACGGAAGATC-5'.
```

The coding strand of the synthetic EK-BGH gene is also provided as sequence ID No. 3. The strand complementary to that of the coding strand, shown supra, has in addition to the sequence shown supra, four nucleotides, 5'-GATX-3', forming the BamHI 5' cohesive end of the complementary strand has been added.

D. DNA Ligation

Two µl (0.2 µg) of the pL110 restriction fragment prepared in Example 1A, 2 µl (8.75 pmoles) of the DNA fragment prepared in Example 1B, and 2 µl (0.1 µg) of the DNA fragment prepared in Example 1C were ligated in a reaction containing 1 µl (10 units) of T4 DNA ligase, 50 mM Tris-HCl (pH 7.6), 10 mM MgCl2, 1 mM dithiothreitol, 1 mM of adenosine 5'-triphosphate and 5% (w/v) polyethylene glycol-8000 in a total volume of 10 µl to construct plasmid pCZR125. A restriction site and function map of plasmid pCZR125 is provided in FIG. 1. The mixture was incubated at 16° C. for 16 hours. A portion of this mixture was used to transform *Escherichia coli* cells as described below.

E. Transformation Procedure

*Escherichia coli* K12 RV308 cells are available from the Northern Regional Research Laboratory, Peoria, Ill. under the accession number NRRL B-15624. A 50 ml culture of *E. coli* K12 RV308 was grown in L-broth (10 g tryptone, 10 g NaCl and 5 g yeast extract per liter of H2O) to an O.D.590 of 0.5 absorbance units. The culture was chilled on ice for ten minutes and then the cells were collected by centrifugation. The cell pellet was resuspended in 25 ml of cold 50 mM CaCl2: mM Tris-HCl (pH 8.0) and incubated on ice for 15 minutes. The cells were collected by centrifugation, the cell pellet was resuspended in 2.5 ml of cold 50 mM CaCl2: 10 mM Tris-HCl (pH 8.0) and the sample was held at 4° C. for 16 hours.

Two hundred µl of this cell suspension was mixed with 50 µl of the ligated DNA prepared above and then incubated on ice for 60 minutes. The mixture was incubated at 32° C. for 45 seconds and then placed on ice for 2 minutes. Five ml of TY medium (1% tryptone, 0.5% yeast extract and 1% sodium chloride, pH 7.4) was added to the mixture and incubation was continued at 32° C. for 2 hours. One hundred µl of this culture was spread on TY agar plates (1% tryptone, 0.5% yeast extract, 1% sodium chloride and 1.5% agar at pH 7.4) that contained 5 µg/ml of tetracycline. These plates were incubated for 16 hours at 32° C. The tetracycline resistant colonies were individually picked and used to inoculate 2 ml of TY medium. The cultures were incubated at 37° C. with aeration for 16 hours.

F. DNA Isolation Procedure

Plasmid DNA was isolated from the culture of transformants as follows. All of the following manipulations were done at ambient temperature unless otherwise indicated. One and a half ml of each of the cultures was transferred to a microcentrifuge tube. The cells were collected by a centrifugation. The supernatant was removed with a fine-tip aspirator and the cell pellet was suspended in 100 µl of a solution containing 50 mM glucose, 10 mM EDTA and 25 mM Tris-HCl (pH 8.0). After incubation at room temperature for 5 minutes, 200 µl of an alkaline sodium dodecyl sulfate (SDS) solution (0.2N NaOH, 1% SDS) was added. The tube was gently inverted to mix and then maintained on ice for 5 minutes. Next, 150 µl of a potassium acetate solution (prepared by adding 11.5 ml of glacial acetic acid and 28.5 ml of water to 60 ml of 5M potassium acetate. The resulting solution is 3M with respect to potassium and 5M with respect to acetate) was added and the contents of the tube mixed by gently vortexing. The sample was kept on ice for 5 minutes and then centrifuged for 10 minutes. The supernatant was transferred to a second centrifuge tube. An equal volume of phenol (saturated with 0.1M Tris (pH 8.0)) was added. The sample was mixed and then centrifuged for 5 minutes. The supernatant was collected and the phenol extraction was repeated. One ml of ice-cold absolute ethanol was added to the supernatant. The sample was mixed and held on dry ice until highly viscous, but not frozen solid. The DNA was then collected by a 5 minute centrifugation. The supernatant was removed by aspiration and 500 µl of 70% ethanol was added to the DNA pellet. The sample was gently vortexed to wash the pellet and centrifuged for 2 minutes. The supernatant was removed and the DNA pellet was dried under vacuum. The DNA was dissolved in 50 µl of TE (10 mM Tris-HCl (pH 8.0) and 1 mM EDTA) and stored at 4° C.

G. Large Scale DNA Isolation

Large amounts of pCZR125 plasmid DNA were isolated as follows. One liter of L broth containing 5 µg/ml tetracycline was inoculated with a colony of *Escherichia coli* RV308/pCZR125. The culture was grown at 32° C. for 16 hours. The culture was centrifuged in a GSA rotor (Sorvall) at 6000 rpm for 5 minutes at 4° C. The resulting supernatant was discarded, and the cell pellet was washed in 40 ml of TES buffer (10 mM Tris-HCl (pH 7.5), 10 mM NaCl, and 1 mM EDTA) and then collected by centrifugation. The supernatant was discarded, and the cell pellet was frozen in a dry ice-ethanol bath and then thawed. The thawed cell pellet was resuspended in 10 ml of a solution of 25% sucrose and 50 mM EDTA. One ml of a 5 mg/ml lysozyme solution, 3 ml of 0.25M EDTA (pH 8.0), and 100 µl of 10 mg/ml boiled RNAse A (available from Sigma Chemical Co., P.O. Box 14508, St. Louis, Mo.) were added to the solution, which was then incubated on ice for 15 minutes. Three ml of lysing solution (prepared by mixing 3 ml of 10% Triton X-100, 75 ml of 0.25M EDTA (pH 8.0), 15 ml of 1M Tris-HCl (pH 8.0), and 7 ml of H$_2$O) were added to the lysozyme treated cells, and the solution was mixed, after which the resulting solution was incubated on ice for another 15 minutes. The lysed cells were frozen in a dry ice-ethanol bath and then thawed.

The cellular debris was removed from the solution by centrifugation at 25,000 rpm for 40 minutes in a SW28.1 rotor (Beckman, Scientific Instrument Division, Campus Drive at Jamboree Blvd., Irvine, CA 92713) and by extraction with buffered phenol. About 30.44 g of CsCl and ~1 ml of a 5 mg/ml ethidiumbromide solution were added to the cell extract, and then the volume of the solution was adjusted to 40 ml with TES buffer (10 mM Tris-HCl (pH 7.5), 10 mM NaCl and 1 mM EDTA). The solution was decanted into a VTi50 ultracentrifuge tube (Beckman), which was then sealed and centrifuged in a VTi50 rotor at 42,000 rpm for about 16 hours. The resulting plasmid band, visualized with ultraviolet light, was isolated and then placed in a Ti75 tube and rotor (Beckman) and centrifuged at 50,000 rpm for 16 hours. Any necessary volume adjustments were made using TES containing 0.761 g/ml CsCl. The plasmid band was again isolated, extracted with salt-saturated 2-propanol to remove ethidium bromide, and diluted 1:3 with TES buffer. One volume of 3M sodium acetate and two volumes of absolute ethanol were then added to the solution, which was then incubated for 16 hours at −20° C. The plasmid DNA was pelleted by centrifuging the solution in a SS34 rotor (Sorvall) for 15 minutes at 10,000 rpm. The plasmid DNA obtained by this procedure was suspended in TE buffer and stored at −20° C.

EXAMPLE 1

Construction of pHPR91

A. Preparation of the 1876 Base Pair EcoRI-ScaI Restriction Fragment of pCZR125

Ten µg of plasmid pCZR125 were digested to completion with 30 units of EcoRI in a 100 µl reaction volume containing 100 µg/ml BSA (bovine serum albumin) 50 mM Tris-HCl (pH 8.0) 10 mM MgCl$_2$, and 100 mM NaCl at 37° C. for one hour. The sample was then incubated at 70° C. for 10 minutes to inactivate the EcoRI.

EcoRI digested plasmid pCZR125 was made blunt-ended by treatment with DNA polymerase I (Klenow Fragment) as follows. Twenty-five µl of the above reaction was adjusted to a 50 µl reaction volume containing 250 µM dATP (deoxyadenosine 5'-triphosphate), 250 µM dCTP (deoxycytosine 5'-triphosphate), 250 µM dGTP (deoxyguanadine 5'-triphosphate), 250 µM TTP (thymidine 5'-triphosphate), 50 mM Tris-HCl (pH 7.8), 10 mM MgCl$_2$, 10 mM β-mercaptoethanol, and 5 units of DNA polymerase I (Klenow Fragment). The sample was incubated at 37° C. for 30 minutes to complete complementary synthesis of the single strand of restriction fragment overhang. Then the reaction mixture was incubated at 70° C. for 15 minutes to inactivate the Klenow Fragment.

The EcoRI digested, Klenow treated pCZR125 plasmid DNA was then digested to completion with ScaI by incubation at 37° C. for one hour in a 150 µl reaction volume containing 50 mM Tris-HCl (pH 8.0), 10 mM MgCl$_2$, 100 mM NaCl, 100 µg/ml BSA and 18 units ScaI. The ScaI was then inactivated by incubating the sample at 70° C. for 10 minutes.

B. Preparation of the 5051 Base Pair AvaI Restriction Fragment of pPR12

The construction of plasmid pPR12 is taught in U.S. Pat. No. 4,436,815, which issued on Mar. 13, 1984 and the teachings of which are herein incorporated by reference.

Ten µg of pPR12 was digested to completion with 30 units of AvaI for one hour at 37° C. in a 100 µl reaction volume containing 100 µg/ml BSA, 50 mM Tris-HCl (pH 8.0), 10 mM MgCl$_2$ and 50 mM NaCl. AvaI was then thermally inactivated by incubation at 70° C. for 15 minutes.

The AvaI digested plasmid pPR12 sample was made blunt ended as follows. Twenty-five µl of the above reaction was adjusted to a 50 µl reaction volume containing 250 µM dATP, 250 µM dCTP, 250 µM dGTP, 250 µM TTP, 50 mM Tris-HCl (pH 7.8), 10 mM MgCl$_2$, 10 mM β-mercaptoethanol, and 5 units of DNA polymerase I (Klenow Fragment). The sample was incubated at 37° C. for 30 minutes to complete complementary synthesis of the single strand of restriction fragment overhang, and then at 70° C. for 15 minutes to inactivate the Klenow Fragment.

C. Final Construction of pHPR91

The DNA samples prepared in Examples 2A and 2B were purified and ethanol co-precipitated as described in Example 1. The DNA was recovered by centrifugation, dried and resuspended in 10 µl of water. The DNA fragments were then ligated by incubating at 4° C. overnight in a 40 µl reaction volume containing 50 mM Tris-HCl (pH 7.8), 10 mM MgCl$_2$, 5 mM DTT (dithiothreitol), 5% glycerol, 0.2 mM adenosine 5'-triphosphate and 40 units of DNA ligase.

A portion of the ligation mixture was used to transform *Escherichia coli* K12 MM294 cells in accordance with the procedure of Example 1E. *E. coli* K12 MM294 cells are available from the American Type Culture Collection, Rockville, Md. 20852 under accession number ATCC 31446. The transformants were selected on L agar containing 10 µg/ml tetracycline. Individual colonies were picked and grown in L broth containing 10 µg/ml tetracycline. Tetracycline resistant transformants containing the desired plasmid pHPR91 were identified following plasmid purification by restriction enzyme analysis. Digestion of plasmid pHPR91 with PvuI yields a 1450 base pair fragment. A restriction site and function map of plasmid pHPR91 is presented in FIG. 2.

EXAMPLE 3

Construction of pHPR97

A. Preparation of EcoRI-BglII Digested pCZR125

Ten µg of pCZR125 DNA was digested to completion with 5 µl (55 units) of EcoRI and 5 µl (55 units) of BglII in a 60 μl reaction volume containing 10 mM Tris-HCl (pH 7.5), 100 mM NaCl, 10 mM MgCl₂, and 10 mM β-mercaptoethanol. The reaction was incubated at 37° C. for two hours. The digested DNA was purified and the 6.0 kb fragment was isolated by preparative agarose gel electrophoresis as described in Example 1A.

B. Preparation of the Transcriptional Activating Sequence DNA

A transcriptional activating sequence was prepared by synthesizing the following single stranded DNA sequences:

(SEQ ID NO: 5)
5'-AATTCGATCTCTCACCTACCAAACAATGCCCCCCTGCAAA
AAATAAATTCATATAAAAAACATACAGATAACCATCTGCG
GTGATAAATTATCTCTGGCGGTGTTGACATAAATACCACT
GGCGGTGATACTGAGCACATCA-3'

(SEQ ID NO: 6)
5'-GATCTGATGTGCTCAGTATCACCGCCAGTGGTATTTATGT
CAACACCGCCAGAGATAATTTATCACCGCAGATGGTTATC
TGTATGTTTTTATATGAATTTATTTTTTGCAGGGGGGCA
TTGTTTGGTAGGTGAGAGATCG-3'

These single stranded DNA segments were synthesized on an automated DNA synthesizer (Applied Biosystems 380B) using β-cyanoethyl phosphoramidite chemistry. The synthetic DNA segments were purified and then stored in TE buffer at 0° C.

Ten μl (5 μg) of each single stranded DNA segment was mixed and heated to 70° C. for 5 minutes. The mixture was cooled at room temperature for 30 minutes to allow the DNA segments to anneal.

The annealed DNA fragment was treated with 1 μl (10 units) of T4 polynucleotide kinase in 70 mM Tris-HCl (pH 7.6), 0.1M KCl, 10 mM MgCl₂, 5 mM DTT containing 0.2 mM adenine 5'-triphosphate in a total volume of 20 μl. The mixture was incubated at 37° C. for thirty minutes. The mixture was then incubated at 70° C. for 5 minutes and then cooled at room temperature.

C. Final Construction of pDHPR97

Figure 3:
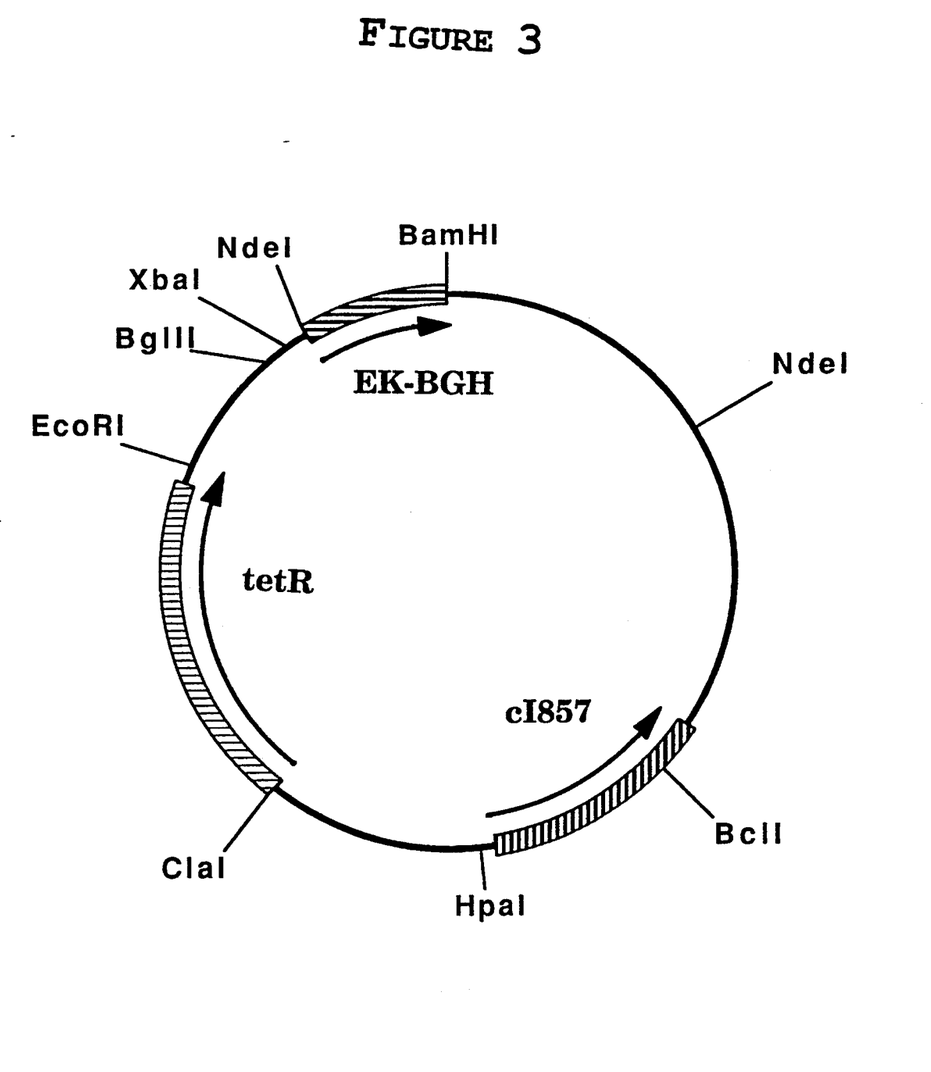
FIG. 3 is a restriction site and function map of plasmid pHPR97.

Two μg of the restriction fragment prepared in Example 3A and 1 μg of the kinased DNA fragment prepared in Example 3B were ligated in substantial accordance with the method of Example 1D, except that the mixture was incubated at room temperature for 1 hour, heated to 70° C. for 5 minutes and then cooled to room temperature. A portion of the ligated DNA was used to transform *Escherichia coli* K12 MM294 cells according to the method of Example 1E. *E. coli* K12 MM294 cells are available from the American Type Culture Collection, Rockville, Md. 20852 under accession number ATCC 3144. Tetracycline resistant transformants were selected and their plasmid DNA was isolated according to the alkaline lysis method described in Example 1F. Restriction analysis was performed to confirm the structure of pHPR97. A restriction site and function map of pHPR97 is presented in FIG. 3.

EXAMPLE 4

Construction of Plasmid pDHKY334

A. Overview

Figure 2:
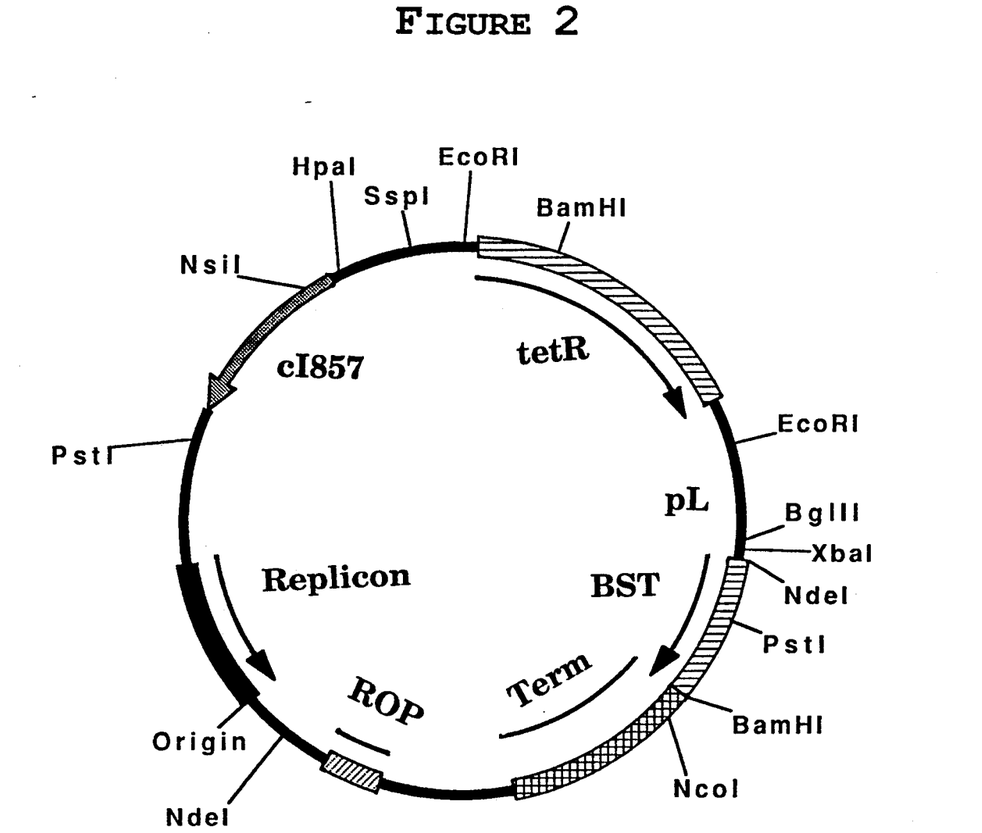
FIG. 2 is a restriction site and function map of plasmid pHPR91.

Plasmid pHKY334 was constructed by replacing the transcriptional activating sequence of plasmid pHPR91 with the transcriptional activating sequence of plasmid pHPR97. Reference to FIG. 2 (pHPR91) and FIG. 3 (pHPR97) illustrates that the construction of plasmid pKHY334 merely requires the double digestion of both pHPR97 and pHPR91 with the restriction endonucleases SalI and XbaI followed by gel isolation and ligation of the large fragment of plasmid pHPR91 and the small fragment of plasmid pHPR97.

B. Preparation of the ~5.718 kb SalI/XbaI fragment of plasmid pHPR91

Approximately 10 μg of pHPR91 was digested to completion in a 50 μl volume of Boehringer Mannheim's Buffer H (50 mM Tris-HCl, 10 mM MgCl₂, 100 mM NaCl, 1 mM dithiothreitol (DDT), pH 7.5 at 37° C. and 100 μg bovine serum albumin) with ~20 U of XbaI and ~20 U of SalI (Boehringer Mannheim). The digest was incubated at 37° C. for ~2 hours. The ~5.718 kb XbaI/SalI fragment of plasmid pHPR91 was isolated from the digestion mixture by agarose gel electrophoresis. The gel was stained in a dilute ethidiumbromide solution and the bands visualized under a 260 nm UV light. A slit was made "above" and "below" the desired bands and a piece of DEAE paper was cut and placed in this slit so it just fit. The gel was returned to the electrophoresis chamber and the DNA was electrophoresed into the paper. The paper was removed to a fresh tube and eluted by the addition of 5 ml of 1.0M NaCl, 10 mM Tris-HCl, pH8. This suspension was filtered through siliconized glass wool packed into a 10 ml syringe that had a 0.45 micron sterilization filter attached (Acrodisc-Gelman Sciences, Incorporated, 600 South Wagner Road, Ann Arbor, Mich. 48106). To the solution 10 ml of 100% ethanol was added and the tube mixed thoroughly. This was placed at −20° C. overnight. The DNA precipitate was recovered by centrifugation in a HB4 rotor (DuPont Sorval) for 20 minutes at 10,000 rpm (4° C.). The DNA pellet was air dried and then resuspended in 100 μl of TE buffer.

C. Preparation of the 0.938 kb SalI/XbaI fragment of plasmid pDHPR97

Approximately 10 μg of plasmid pHPR97 was digested with SalI and XbaI in substantial accordance with the method of Example 4B. The 0.938 kb SalI/XbaI fragment of plasmid pHPR97 was then gel purified, extracted and precipitated as described in Example 4B.

D. Ligation of the ~5.817 kb SalI/XbaI fragment of plasmid pHPR91(Example 4B) with the ~0.938 kb SalI/XbaI fragment of plasmid pHPR97 (Example 4E) to generate desired plasmid pHKR334.

Approximately ~0.6 μg of the plasmid pHPR91 derived fragment was ligated with ~0.3 μg of the plasmid pHPR97 derived fragment. The DNAs were co-precipitated, air dried, and resuspended in 10 μl of (30 mM tris-HCl, pH 7.5, 0.5 mM ATP, 10 mM DTT, 6 mM MgCl₂, and 1 U of T4 ligase (Boehringer Mannheim).

pHKY334 was generated upon the ligation of the pHPR91 and pHPR97 fragments described above.

E. Transformation of *E. coli* RV308 with plasmid pHKY334

The transformation process proceeded in substantial accordance with the teachings of Example 1E. Individual colonies of transformants were picked and grown in L broth containing 10 μg/ml tetracycline. Restriction endonuclease mapping and DNA sequencing were used to confirm the identity of plasmid pKHY334. A restriction site and function map of plasmid pHKY334 is provided in FIG. 4.

---

We claim:
1. Plasmid pHKY334, which is NRRL B-21095.
2. A host cell transformed with the plasmid pHKY334.
3. The transformed hose cell of claim 2 that is *E. Coli* RV308/pHKY334, which is NRRL B-21095.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

```
CTAGAGGGTA TTAATAATGT ATATTGATTT TAATAAGGAG GAATAATCA         49
```

( 2 ) INFORMATION FOR SEQ ID NO:2:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

```
TATGATTATT CCTCCTTATT AAAATCAATA TACATTATTA ATACCCT            47
```

( 2 ) INFORMATION FOR SEQ ID NO:3:

( i ) SEQUENCE CHARACTERISTICS:
        ( A ) LENGTH: 601 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 2..601

( x i ) SEQUENCE DESCRIPTION: SEQ ID NO:3:

```
T   ATG TTC CCA TTG GAT GAT GAT GAT AAG TTC CCA GCC ATG TCC TTG      46
    Met Phe Pro Leu Asp Asp Asp Asp Lys Phe Pro Ala Met Ser Leu
    1               5                   10                  15

TCC GGC CTG TTT GCC AAC GCT GTG CTC CGG GCT CAG CAC CTG CAT CAG      94
Ser Gly Leu Phe Ala Asn Ala Val Leu Arg Ala Gln His Leu His Gln
                20                  25                  30

CTG GCT GCT GAC ACC TTC AAA GAG TTT GAG CGC ACC TAC ATC CCG GAG     142
Leu Ala Ala Asp Thr Phe Lys Glu Phe Glu Arg Thr Tyr Ile Pro Glu
            35                  40                  45

GGA CAG AGA TAC TCC ATC CAG AAC ACC CAG GTT GCC TTC TGC TTC TCT     190
Gly Gln Arg Tyr Ser Ile Gln Asn Thr Gln Val Ala Phe Cys Phe Ser
        50                  55                  60

GAA ACC ATC CCG GCC CCC ACG GGC AAG AAT GAG GCC CAG CAG AAA TCA     238
Glu Thr Ile Pro Ala Pro Thr Gly Lys Asn Glu Ala Gln Gln Lys Ser
    65                  70                  75

GAC TTG GAG CTG CTT CGC ATC TCA CTG CTC CTC ATC CAG TCG TGG CTT     286
Asp Leu Glu Leu Leu Arg Ile Ser Leu Leu Leu Ile Gln Ser Trp Leu
80                  85                  90                  95

GGG CCC CTG CAG TTC CTC AGC AGA GTC TTC ACC AAC AGC TTG GTG TTT     334
Gly Pro Leu Gln Phe Leu Ser Arg Val Phe Thr Asn Ser Leu Val Phe
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     |     | 100 |     |     |     |     | 105 |     |     |     |     | 110 |     |     |
| GGC | ACC | TCG | GAC | CGT | GTC | TAT | GAG | AAG | CTG | AAG | GAC | CTG | GAG | GAA | GGC | 382 |
| Gly | Thr | Ser | Asp | Arg | Val | Tyr | Glu | Lys | Leu | Lys | Asp | Leu | Glu | Glu | Gly |
|     |     |     | 115 |     |     |     |     | 120 |     |     |     |     | 125 |     |     |
| ATC | CTG | GCC | CTG | ATG | CGG | GAG | CTG | GAA | GAT | GGC | ACC | CCC | CGG | GCT | GGG | 430 |
| Ile | Leu | Ala | Leu | Met | Arg | Glu | Leu | Glu | Asp | Gly | Thr | Pro | Arg | Ala | Gly |
|     |     | 130 |     |     |     |     | 135 |     |     |     |     | 140 |     |     |     |
| CAG | ATC | CTC | AAG | CAG | ACC | TAT | GAC | AAA | TTT | GAC | ACA | AAC | ATG | CGC | AGT | 478 |
| Gln | Ile | Leu | Lys | Gln | Thr | Tyr | Asp | Lys | Phe | Asp | Thr | Asn | Met | Arg | Ser |
|     | 145 |     |     |     |     | 150 |     |     |     |     | 155 |     |     |     |     |
| GAC | GAC | GCG | CTU | CTC | AAG | AAC | TAC | GGT | CTG | CTC | TCC | TGC | TTC | CGG | AAG | 526 |
| Asp | Asp | Ala | Leu | Leu | Lys | Asn | Tyr | Gly | Leu | Leu | Ser | Cys | Phe | Arg | Lys |
| 160 |     |     |     |     | 165 |     |     |     |     | 170 |     |     |     |     | 175 |
| GAC | CTG | CAT | AAG | ACG | GAG | ACG | TAC | CTG | AGG | GTC | ATG | AAG | TGC | CGC | CGC | 574 |
| Asp | Leu | His | Lys | Thr | Glu | Thr | Tyr | Leu | Arg | Val | Met | Lys | Cys | Arg | Arg |
|     |     |     |     | 180 |     |     |     |     | 185 |     |     |     |     | 190 |     |
| TTC | GGG | GAG | GCC | AGC | TGT | GCC | TTC | TAG |     |     |     |     |     |     |     | 601 |
| Phe | Gly | Glu | Ala | Ser | Cys | Ala | Phe |
|     |     |     |     | 195 |     |     |     | 200 |

( 2 ) INFORMATION FOR SEQ ID NO:4:

( i ) SEQUENCE CHARACTERISTICS:
        ( A ) LENGTH: 199 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:4:

| Met | Phe | Pro | Leu | Asp | Asp | Asp | Lys | Phe | Pro | Ala | Met | Ser | Leu | Ser |
| --- | --- | --- | --- | --- | --- | --- | --- | --- | --- | --- | --- | --- | --- | --- |
| 1 |     |     |     | 5 |     |     |     |     | 10 |     |     |     |     | 15 |
| Gly | Leu | Phe | Ala | Asn | Ala | Val | Leu | Arg | Ala | Gln | His | Leu | His | Gln | Leu |
|     |     |     | 20 |     |     |     |     | 25 |     |     |     |     | 30 |     |     |
| Ala | Ala | Asp | Thr | Phe | Lys | Glu | Phe | Glu | Arg | Thr | Tyr | Ile | Pro | Glu | Gly |
|     |     | 35 |     |     |     |     | 40 |     |     |     |     | 45 |     |     |     |
| Gln | Arg | Tyr | Ser | Ile | Gln | Asn | Thr | Gln | Val | Ala | Phe | Cys | Phe | Ser | Glu |
|     | 50 |     |     |     |     | 55 |     |     |     |     | 60 |     |     |     |     |
| Thr | Ile | Pro | Ala | Pro | Thr | Gly | Lys | Asn | Glu | Ala | Gln | Gln | Lys | Ser | Asp |
| 65 |     |     |     |     | 70 |     |     |     |     | 75 |     |     |     |     | 80 |
| Leu | Glu | Leu | Leu | Arg | Ile | Ser | Leu | Leu | Leu | Ile | Gln | Ser | Trp | Leu | Gly |
|     |     |     |     | 85 |     |     |     |     | 90 |     |     |     |     | 95 |     |
| Pro | Leu | Gln | Phe | Leu | Ser | Arg | Val | Phe | Thr | Asn | Ser | Leu | Val | Phe | Gly |
|     |     |     | 100 |     |     |     |     | 105 |     |     |     |     | 110 |     |     |
| Thr | Ser | Asp | Arg | Val | Tyr | Glu | Lys | Leu | Lys | Asp | Leu | Glu | Glu | Gly | Ile |
|     |     |     | 115 |     |     |     |     | 120 |     |     |     |     | 125 |     |     |
| Leu | Ala | Leu | Met | Arg | Glu | Leu | Glu | Asp | Gly | Thr | Pro | Arg | Ala | Gly | Gln |
|     |     | 130 |     |     |     |     | 135 |     |     |     |     | 140 |     |     |     |
| Ile | Leu | Lys | Gln | Thr | Tyr | Asp | Lys | Phe | Asp | Thr | Asn | Met | Arg | Ser | Asp |
| 145 |     |     |     |     | 150 |     |     |     |     | 155 |     |     |     |     | 160 |
| Asp | Ala | Leu | Leu | Lys | Asn | Tyr | Gly | Leu | Leu | Ser | Cys | Phe | Arg | Lys | Asp |
|     |     |     |     | 165 |     |     |     |     | 170 |     |     |     |     | 175 |     |
| Leu | His | Lys | Thr | Glu | Thr | Tyr | Leu | Arg | Val | Met | Lys | Cys | Arg | Arg | Phe |
|     |     |     | 180 |     |     |     |     | 185 |     |     |     |     | 190 |     |     |
| Gly | Glu | Ala | Ser | Cys | Ala | Phe |
|     |     | 195 |

( 2 ) INFORMATION FOR SEQ ID NO:5:

( i ) SEQUENCE CHARACTERISTICS:
        ( A ) LENGTH: 142 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:5:

AATTCGATCT CTCACCTACC AAACAATGCC CCCCTGCAAA AAATAAATTC ATATAAAAAA    60

CATACAGATA ACCATCTGCG GTGATAAATT ATCTCTGGCG GTGTTGACAT AAATACCACT   120

GGCGGTGATA CTGAGCACAT CA   142

(2) INFORMATION FOR SEQ ID NO:6:

(i) SEQUENCE CHARACTERISTICS:
(A) LENGTH: 142 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

GATCTGATGT GCTCAGTATC ACCGCCAGTG GTATTTATGT CAACACCGCC AGAGATAATT    60

TATCACCGCA GATGGTTATC TGTATGTTTT TTATATGAAT TTATTTTTTG CAGGGGGGCA   120

TTGTTTGGTA GGTGAGAGAT CG   142